United States Patent [19]

Lasser

[11] 4,335,203

[45] Jun. 15, 1982

[54] METHOD FOR IDENTIFYING POTENTIAL CONTRAST MEDIA REACTORS

[75] Inventor: Elliott C. Lasser, La Jolla, Calif.

[73] Assignee: The Regents of the University of California, Berkeley, Calif.

[21] Appl. No.: 167,278

[22] Filed: Jul. 10, 1980

[51] Int. Cl.³ .............................................. C12Q 1/38
[52] U.S. Cl. ..................................... 435/23; 435/810; 424/5
[58] Field of Search ..................... 23/230 B; 424/4, 5; 435/13, 23, 24, 810, 296

[56] References Cited

U.S. PATENT DOCUMENTS

| 3,404,143 | 10/1968 | Hebky et al. | 424/4 |
| 4,038,147 | 7/1977 | Reno | 435/13 |
| 4,252,902 | 2/1981 | Fujii et al. | 435/213 |

FOREIGN PATENT DOCUMENTS 5036759  3/1980 Japan ..................................... 435/4

OTHER PUBLICATIONS

Kluft, "Determination of Prekallikrein in Human Plasma:" J. Lab. Clin. Med. Jan. 1978, pp. 83–95.
Stormorken et al., *Haemostasis*, 1978, 7: 69–75.
Gjonnaess, *Haemorrn*, 1972, 28: 182–193.
Griffin et al., *Seminars in Thrombosis & Hemostasis*, 5: 54–273; 1979.

*Primary Examiner*—Peter A. Hruskoci
*Attorney, Agent, or Firm*—Bertram I. Rowland

[57] ABSTRACT

Method and kit are provided for determining hypersensitivity, particularly to polyiodinated contrast media. Plasma is combined with a prekallikrein activator and a substrate capable of providing a detectible signal and the proteolytic activity measured by determining the signal level by means of the transformation of said substrate.

4 Claims, No Drawings

METHOD FOR IDENTIFYING POTENTIAL CONTRAST MEDIA REACTORS

The invention described herein was made in the course of, or under a grant from, the U.S. Public Health Service.

BACKGROUND OF THE INVENTION

1. Field of the Invention

Contrast media are widely used in x-ray examination. A substantial proportion of the contrast media employed is water soluble polyiodinated aromatic compounds having a variety of water soluble annular substituents. A significant portion of the population has an adverse reaction to the x-ray contrast material. Testing, when done, has been accomplished by subjecting the patient to a small intravascular injection of the contrast medium, but the discriminate potential of this test is low and some patients succumb to the test dose itself.

It would therefore be desirable to have a simple rapid test for screening patients to whom x-ray contrast media will be administered.

2. Description of the Prior Art

Kluft, J. Lab. and Clin. Med. (1978), 91:83–95 discloses an assay for prekallikrein, disclosing a number of activators including dextran sulfate, and employing a chromogenic substrate. Stormorken et al., Haemostasis (1978) 7:69–75 discloses alternative techniques for assaying prekallikrein.

Promoters for prekallikrein are also described in Gjonnaess, Haemorrn 28:182–193, 1972; and Griffin and Cochrane, Seminars in Thrombosis and Hemostasis, 5:54–273, 1979.

SUMMARY OF THE INVENTION

Method and kit are employed for screening hypersensitivity in patients, particularly sensitivity to x-ray polyiodinated contrast media, wherein the plasma of the patient is assayed for rate of prekallikrein activation in the presence of an activator. The kallikrein formed is assayed employing a kallikrein substrate which provides for a detectable signal. The rate of development of protease activity is predictive of the likelihood of an adverse reaction.

DESCRIPTION OF THE SPECIFIC EMBODIMENTS

Patients are tested for hypersensitivity, particularly to x-ray contrast media, including polyiodinated aromatic compounds substituted with water solubilizing groups. The test employs a plasma sample from a patient who may or may not have had a prior hypersensitive response. Conveniently, the plasma sample may be subjected to citration and siliconizing (silicone coated container). Citrate concentrations will generally vary from about 0.05 to 0.2 M.

The plasma sample is then combined with a prekallikrein activator. Various activators are known, such as dextran sulfate (of from about 200,000 to 1,000,000 molecular weight, desirably of about 500,000 molecular weight) kaolin, glass, ellagic acid, cellulose sulfate, and chondroitin. Of these activators, dextran sulfate is particularly useful, since it is clear, commercially available, efficient, and at the concentrations employed does not interfere with the measurement of protease activity. The plasma sample is combined with the activator at an appropriate concentration to provide for a convenient rate for measurement.

When using dextran sulfate, the final concentration of dextran sulfate will vary from about 0.5 to 3 mg/l., more usually about 1 mg/l. The plasma activator and plasma are combined at a temperature below about 10° C., preferably at about 0° C. Plasma usually has inhibitors of kallikrein. At the lower temperatures, it is found that inhibition is substantially reduced. Usually the period of time for activation should be at least about 10 min, preferably at least about 15 min, more usually at least about 30 min, and usually not exceeding about one hour. After a sufficient incubation period, the activated prekallikrein-kallikrein-solution is transferred to an appropriately buffered solution of substrate at a pH in the range of about 6 to 9 and the enzymatic rate determined at a temperature in the range of about 20° to 40° C. Readings may be taken over about 0.5 to 5 min.

The substrate can be widely varied. Particularly convenient are chromogenic substrates which may be spectrophotometrically monitored. Illustrative substrates include chromozym PK, Pentapharm AG, Basel, Switzerland; S-2251, Ab Kabi, Stockholm, Sweden, and PPAN, Pentapharm AG, Basel, Switzerland. PPAN is $\alpha$-N-benzoyl-L-proline-L-phenylalanine-L-arginine-p-nitroanilide. The concentration of enzyme substrate employed will be sufficiently high so as to be substantially non-limiting on the rate. In effect, the rate will be zero order in substrate. Concentrations will generally vary from about 0.1 to 10 mM, usually 0.5 to 5 mM.

It has been found that measurement of prekallikrein activation in plasma can be related to sensitivity to x-ray contrast media. Citrated siliconized plasma samples (9 volumes plasma with 1 volume 0.2 M citrate) were combined at 0° with equal volumes of dextran sulfate solution to provide a final concentration of 1.25 mg/l. dextran sulfate and allowed to stand for 30 min. A 15 $\mu$l aliquot was dissolved in 1 mM PPAN in pH7.9 buffer and the rate of change in optical density (OD/min) at 405 nm at 37° C. determined. The results are reported in units, where one unit equals 0.00010 D/min. Of 39 samples, 17 known contrast material reactors (sensitive) and 22 confirmed contrast material non-reactors (non-sensitive), it was found that the average change in the sensitive group was 414 with a standard deviation of 202 and a standard error 49.01. The 22 non-reactors showed corresponding values of an average change of 146.3, a standard deviation of 69.6 and a standard error of 14.85. The means of these two groups differed by P less than 0.001.

The results of the assay of the two groups may be looked at in another way. The changes in OD/min. were arbitrarily divided into five groups as follows:

TABLE 1

|  | Reactors | Non-Reactors |
| --- | --- | --- |
| 0–200 | 2 | 18 |
| 200–400 | 7 | 4 |
| 400–600 | 4 | 0 |
| 600–800 | 3 | 0 |
| 800–1000 | 1 | 0 |

Utilizing an arbitrary cutoff of 200, it is found that the predictive value equals 79%, the sensitivity equals 79%, and the specificity equals 60%. If less than 400 is considered the cutoff, the sensitivity is 30% and the specificity 100%.

It is evident from the above results that a simple and rapid screening method is provided for patients to be treated with x-ray contrast media.

For convenience and enhanced accuracy, kits can be provided having the necessary containers and reagents to provide efficiency and accuracy in performing the subject determination, while simplifying the protocol. The kit would comprise a siliconized blood collection tube, containing one volume of 0.2 M citrate (usually sodium) into which 9 volumes of blood are to be drawn. The tube volume will be sufficient to hold 1 to 10 ml, usually at least 5 ml. Usually the final volume will be 5 ml. A second inert container is provided of about 2 ml capacity, containing 0.5 ml of 2.5 µg/ml dextran sulfate (MW, 500,000 daltons) in 5 mM pH7.4 phosphate. The container should have a 1 ml graduation.

Two disposable plastic transfer pipets are provided: a 2 ml dropper and a 15 µl pipet.

Finally, a plastic stoppered cuvette is provided for use in a spectrophotometer, usually of a volume of about 0.5 to 5 ml, more usually about 1 to 3 ml. The cuvette will contain sufficient kallikrein substrate so as not to be rate limiting. Desirably, when PPAN is employed the amount will be sufficient to provide a concentration of at least about $1 \times 10^{-3}$ M in a 1 ml sample. The solution will be buffered to pH7.9 or contain sufficient solid buffer so that upon dilution the assay solution is appropriately buffered.

Following collection in the citrated siliconized tube, the plasma is separated by centrifugation, cooled to 0° C., and 0.5 ml transferred with the plastic dropper to the 0.5 ml dextran sulfate solution, also cooled to 0° C. After the predetermined time for activation, usually 30 min, an aliquot, usually 15µl is transferred to the PPAN solution, usually about 1 µl, in the cuvette, and the change in optical density with time determined, usually 3 min. The change in optical density per minute (OD/min) times $10^4$ will be calculated. This is the desired quantity for assessing the potential for reaction to contrast media.

Although the foregoing invention has been described in some detail by way of illustration and example for purposes of clarity of understanding, it will be obvious that certain changes and modifications may be practiced within the scope of the appended claims.

What is claimed is:

1. In a method of administering an iodinated X-ray contrast medium to a host, of the type wherein the host is tested for sensitivity to said contrast medium before internal administration, the improvement comprising:

assaying for prekallikrein activation by combining a prekallikrein activator with plasma sample of said host to produce kallikrein;

determining the kallikrein activity in said plasma sample over a predetermined period of time by combining said plasma sample with a kallikrein substrate under conditions effective for measuring said activity;

comparing the kallikrein activity obtained to the kallikrein activity in a host known to be sensitive to said contrast medium to determine said sensitivity.

2. A method according to claim 1, wherein said assaying includes activating prekallikrein with dextran sulfate at a temperature from about 0° to 10° C. for a time in the range of about 10 mins. to 60 mins.

3. A method according to claim 2, wherein the time is about 30 mins.

4. A method according to claims 2 or 3, wherein a-N-benzoyl-L-proline-L-phenylalanine-L-arginine-p-nitroanilide is employed as said kallikrein substrate.

* * * * *